(12) United States Patent
Kang

(10) Patent No.: US 11,219,591 B2
(45) Date of Patent: Jan. 11, 2022

(54) EAR-CLEANSING AGENT FOR COMPANION ANIMALS AND METHOD OF MANUFACTURING THE SAME

(71) Applicant: KOONA ENT CO., LTD., Seoul (KR)

(72) Inventor: Jun Bae Kang, Seoul (KR)

(73) Assignee: KOONA ENT CO., LTD., Seoul (KR)

( * ) Notice: Subject to any disclaimer, the term of this patent is extended or adjusted under 35 U.S.C. 154(b) by 380 days.

(21) Appl. No.: 16/303,843

(22) PCT Filed: Jun. 15, 2017

(86) PCT No.: PCT/KR2017/006247
§ 371 (c)(1),
(2) Date: Nov. 21, 2018

(87) PCT Pub. No.: WO2018/143520
PCT Pub. Date: Aug. 9, 2018

(65) Prior Publication Data
US 2020/0315948 A1  Oct. 8, 2020

(30) Foreign Application Priority Data
Feb. 2, 2017 (KR) .......................... 10-2017-0015062

(51) Int. Cl.
| | | |
|---|---|---|
| *A61K 8/9767* | (2017.01) | |
| *A61K 8/34* | (2006.01) | |
| *A61K 8/365* | (2006.01) | |
| *A61K 8/368* | (2006.01) | |
| *A61K 8/41* | (2006.01) | |
| *A61K 8/44* | (2006.01) | |
| *A61K 36/15* | (2006.01) | |
| *A61Q 19/10* | (2006.01) | |
| *B01D 11/02* | (2006.01) | |

(52) U.S. Cl.
CPC ............ *A61K 8/9767* (2017.08); *A61K 8/342* (2013.01); *A61K 8/365* (2013.01); *A61K 8/368* (2013.01); *A61K 8/41* (2013.01); *A61K 8/44* (2013.01); *A61K 36/15* (2013.01); *A61Q 19/10* (2013.01); *A61K 2236/15* (2013.01); *A61K 2236/17* (2013.01); *A61K 2236/37* (2013.01); *B01D 11/0296* (2013.01)

(58) Field of Classification Search
None
See application file for complete search history.

(56) References Cited

U.S. PATENT DOCUMENTS

2009/0068255 A1 * 3/2009 Yu .................. A61Q 19/005
424/450

FOREIGN PATENT DOCUMENTS

| KR | 10-0429277 B1 | 4/2004 |
|---|---|---|
| KR | 10-0796994 B1 | 1/2008 |
| KR | 10-1437336 B1 | 9/2014 |
| KR | 10-2015-0003073 A | 1/2015 |
| KR | 10-1534384 B1 | 7/2015 |
| KR | 10-2016-0004878 A | 1/2016 |

* cited by examiner

*Primary Examiner* — Terry A McKelvey
*Assistant Examiner* — Catheryne Chen
(74) *Attorney, Agent, or Firm* — Novick, Kim & Lee, PLLC; Sang Ho Lee

(57) ABSTRACT

The present invention relates to an ear-cleansing agent for companion animals and a method of manufacturing the same. More particularly, the present invention relates to an ear-cleansing agent for companion animals, which includes distilled *Chamaecyparis obtusa* water extracted from *Chamaecyparis obtusa* trees so as to enable antibacterial action, deodorization, and exfoliation and which does not include a surfactant so that the skin is not irritated even when the ear-cleansing agent is not washed away using water, and a method of manufacturing the same.

2 Claims, 3 Drawing Sheets

EAR-CLEANSING AGENT FOR COMPANION ANIMALS AND METHOD OF MANUFACTURING THE SAME

TECHNICAL FIELD

The present invention relates to an ear-cleansing agent for companion animals and a method of manufacturing the same. More particularly, the present invention relates to an ear-cleansing agent for companion animals, which includes distilled *Chamaecyparis obtusa* water extracted from *Chamaecyparis obtusa* trees so as to enable antibacterial action, deodorization, and exfoliation and which does not include a surfactant so that the skin is not irritated even when the ear-cleansing agent is not washed away using water, and a method of manufacturing the same.

BACKGROUND ART

Companion animals are animals that are raised at home for a person to emotionally depend thereon. In the past, the term "pet" was often used to indicate that such an animal is cute and pleasing to persons. However, such animals have come to be called companion animals with growing awareness that animals are not toys but companions living together with persons. Examples of companion animals include mammals such as hamsters, birds such as parrots and canaries, fish such as goldfishes and tropical fishes, and reptiles such as iguanas and chameleons, in addition to dogs and cats.

In recent years, particularly, increasing numbers of dogs and cats have been living together in the same space as humans. Accordingly, the importance of hygiene and cleanliness has increased, and there is increasing need for the development of cleansing agents for companion animals only, which do not irritate the skin of companion animals.

Patent Document

Korean Patent no. 10-1534384 (registered on Jul. 9, 2015) "Cleansing agent composition for pets and method of manufacturing the same"

However, since a conventional cleansing agent for pets contains a surfactant, the cleansing agent must be thoroughly removed using water. In particular, when the cleansing agent is used as an ear-cleansing agent, the ear of the companion animal must be washed clean with water. However, it is difficult to clean the ear stained with the cleansing agent using water due to the characteristics of companion animals. In addition, when the cleansing agent remaining in the ear is not washed clean using water, the skin of the companion animal becomes irritated, causing swollen red skin or inflammation.

DISCLOSURE

Technical Problem

The present invention has been made keeping in mind the above problems occurring in the prior art, and an object of the present invention is to provide an ear-cleansing agent for companion animals, which does not include a surfactant so that the skin is not irritated even when the ear-cleansing agent is not washed away using water.

It is another object of the present invention to provide an ear-cleansing agent for companion animals, which includes distilled *Chamaecyparis obtusa* water extracted from *Chamaecyparis obtusa* trees so as to enable antibacterial action, deodorization, and exfoliation.

It is a further object of the present invention to provide an ear-cleansing agent for companion animals that enables complete cleansing even without washing with water during ear cleansing, thereby securing easy use thereof.

Technical Solution

In order to accomplish the above objects, the present invention is embodied by embodiments having the following constitutions.

According to an embodiment of the present invention, an ear-cleansing agent for companion animals according to the present invention includes a *Chamaecyparis obtusa* sap extracted from *Chamaecyparis obtusa* trees as an effective component.

According to another embodiment of the present invention, in the ear-cleansing agent for companion animals according to the present invention, the *Chamaecyparis obtusa* sap is distilled *Chamaecyparis obtusa* water that is extracted via steps of: drying *Chamaecyparis obtusa* trees in a dryer and then cutting the dried *Chamaecyparis obtusa* trees to perform powderization, placing the powderized *Chamaecyparis obtusa* trees in a distillation tank to thus supply distilled water, heating the distillation tank to thus supply steam to the powderized *Chamaecyparis obtusa* trees so that water vapor containing a component extracted from the steam is moved to a cooler, thus extracting *Chamaecyparis obtusa* oil and the distilled *Chamaecyparis obtusa* water, and separating and extracting the distilled *Chamaecyparis obtusa* water from an extract obtained by extracting the *Chamaecyparis obtusa* oil and the distilled *Chamaecyparis obtusa* water.

According to another embodiment of the present invention, the ear-cleansing agent for companion animals according to the present invention includes:

a solvent, a humectant, a pH adjuster, a sterilizing preservative, and an exfoliating agent in the distilled *Chamaecyparis obtusa* water, so that antibacterial action, deodorization, and exfoliation are capable of being performed without irritating the skin even when the ear-cleansing agent is not washed away using water.

According to another embodiment of the present invention, the ear-cleansing agent for companion animals according to the present invention includes purified water as the solvent, glycerin and panthenol as the humectant, malic acid and tromethamine as the pH adjuster, benzoic acid as the sterilizing preservative, and salicylic acid as the exfoliating agent.

According to another embodiment of the present invention, the ear-cleansing agent for companion animals according to the present invention includes:

46 to 50 parts by weight of the distilled *Chamaecyparis obtusa* water, 40 to 55 parts by weight of the purified water, 3 to 7 parts by weight of the glycerin, 0.3 to 0.6 parts by weight of the panthenol, 1 to 3 parts by weight of the malic acid, 1 to 3 parts by weight of the tromethamine, 0.1 to 0.2 parts by weight of the benzoic acid, and 0.02 to 0.06 parts by weight of the salicylic acid.

According to another embodiment of the present invention, a method of manufacturing an ear-cleansing agent for companion animals according to the present invention includes a heating-agitation step of performing heating while mixing purified water, malic acid, benzoic acid, and salicylic acid to perform dissolution, a cooling-agitation step of cooling and agitating a mixed solution obtained after the heating-agitation step is completed, and a raw-material-mixing step of mixing the cooled and agitated mixed solution with distilled *Chamaecyparis obtusa* water, glycerin, panthenol, and tromethamine.

According to another embodiment of the present invention, the heating-agitation step of the method of manufacturing the ear-cleansing agent for companion animals according to the present invention includes heating to 75 to 85° C., and the cooling-agitation step includes cooling to 30 to 38° C.

According to another embodiment of the present invention, in the method of manufacturing the ear-cleansing agent for companion animals according to the present invention, 40 to 55 parts by weight of the purified water, 1 to 3 parts by weight of the malic acid, 0.3 to 0.6 parts by weight of the benzoic acid, and 0.02 to 0.06 parts by weight of the salicylic acid are mixed in the heating-agitation step, and 46 to 50 parts by weight of the distilled *Chamaecyparis obtusa* water, 3 to 7 parts by weight of the glycerin, 0.3 to 0.6 parts by weight of the panthenol, and 1 to 3 parts by weight of the tromethamine are mixed in the raw-material-mixing step.

According to another embodiment of the present invention, the method of manufacturing the ear-cleansing agent for companion animals according to the present invention further includes a filtration step of eliminating foreign materials from a mixture obtained after the raw-material-mixing step is completed.

Advantageous Effects

The present invention may obtain the following effects by the combination of the above-described embodiments with the constitution that will be described below, and the use relationship thereof.

In the present invention, since a surfactant is not used in an ear-cleansing agent for companion animals, there is no irritation to the skin even when the ear-cleansing agent is not washed away using water, thereby securing an effect of low skin irritation.

In the present invention, distilled *Chamaecyparis obtusa* water is used to thus enable antibacterial action, deodorization, and exfoliation, whereby the present invention is effective as a cleansing agent.

In the present invention, cleansing of the ear of the companion animal is completed without washing with water, thereby securing easy use.

BEST MODE

Figure 1:
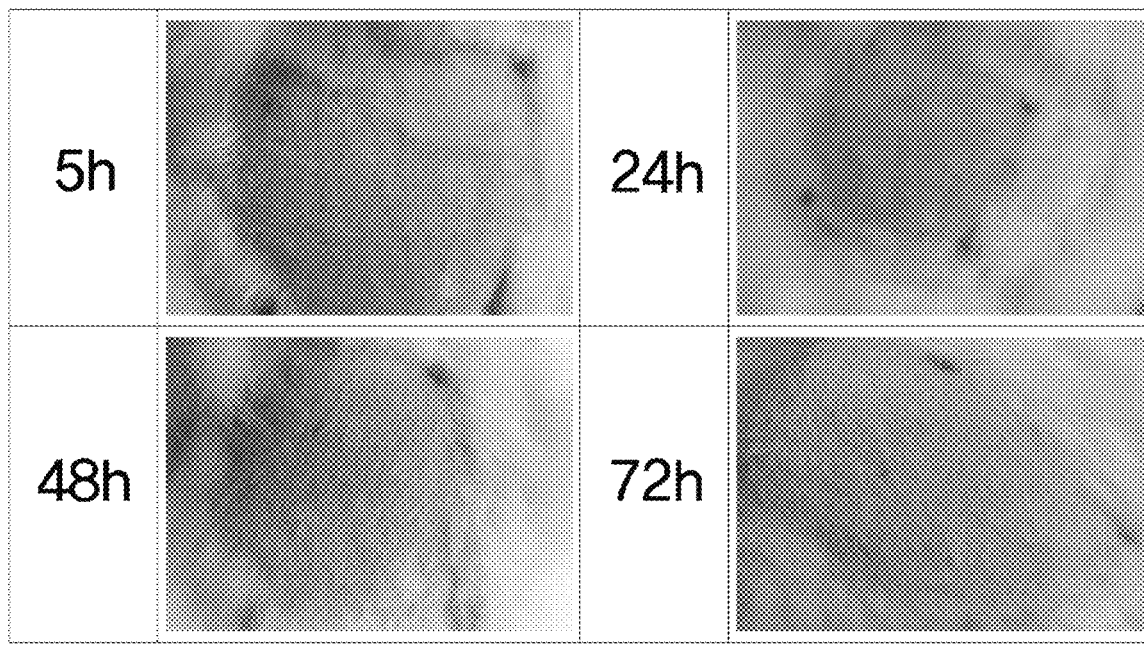
FIG. 1 is a photograph showing the result of an experiment on the degree of skin irritation.

Hereinafter, an ear-cleansing agent for companion animals according to the present invention will be described in detail with reference to the accompanying drawings. Unless defined otherwise, all terms used in the present specification are synonymous with the generic meanings of the terms as understood by those of ordinary skill in the art to which the present invention belongs, and if the generic meaning conflicts with the meaning of the terms used in the present specification, the terms are as defined in the present specification. Further, a detailed description of known functions and configurations that may unnecessarily obscure the gist of the present invention will be omitted.

Unless defined otherwise, all terms (including technical and scientific terms) used in the present specification are to be understood as those commonly understood by those of ordinary skill in the art to which the present invention belongs. Also, the terms defined in generally used dictionaries should not be ideally or excessively interpreted unless clearly defined otherwise herein. Throughout the specification, when any portion "includes" any component, this means that the portion does not exclude other components but may further include other components unless otherwise stated.

In the present invention, companion animals mean mammals such as dogs, cats, rabbits, and hamsters.

An ear-cleansing agent for companion animals according to an embodiment of the present invention includes *Chamaecyparis obtusa* sap extracted from *Chamaecyparis obtusa* trees as an effective component.

The *Chamaecyparis obtusa* trees are evergreen tall-trees of Cupressaceae of Coniferales of gymnosperms, which originate in Japan but are widely cultivated as a farmed tree species in the southern part of Korea through development thereof. *Chamaecyparis obtusa* trees are used for their deodorizing and antimicrobial properties due to the unique fragrance thereof.

The *Chamaecyparis obtusa* sap of the present invention adopts distilled *Chamaecyparis obtusa* water that is extracted via steps of: drying *Chamaecyparis obtusa* trees, including leaves and stems, in a dryer and then cutting the dried *Chamaecyparis obtusa* trees to perform powderization, placing the powderized *Chamaecyparis obtusa* trees in a distillation tank to thus supply distilled water, heating the distillation tank to thus supply steam to the powderized *Chamaecyparis obtusa* trees so that water vapor containing a component extracted from the steam is moved to a cooler, thus extracting *Chamaecyparis obtusa* oil and the distilled *Chamaecyparis obtusa* water, and separating and extracting the distilled *Chamaecyparis obtusa* water from an extract obtained by extracting the *Chamaecyparis obtusa* oil and the distilled *Chamaecyparis obtusa* water.

When the *Chamaecyparis obtusa* trees are heated in the distillation tank to perform extraction, the *Chamaecyparis obtusa* oil and the *Chamaecyparis obtusa* sap are extracted. The *Chamaecyparis obtusa* oil contains the effective component, but this component is in the form of oil. In order to use the oily component as a component of the ear-cleansing agent, there is a problem in that a surfactant needs to be used in order to perform dissolution in water. Accordingly, only the *Chamaecyparis obtusa* sap is separated and then used.

A surfactant is a compound having a hydrophilic part which is easy to dissolve in water and a hydrophobic part which is easy to dissolve in oil. Surfactants help mix water and oil with each other and may thus eliminate contaminants, and are therefor frequently used in soaps and detergents. Surfactants are used in general cleansing agents such as soaps or body cleansers, and components derived from residues remaining after refining crude oil are used therein. Accordingly, surfactants have problems in that proteins may be denatured and the skin may be irritated due to the high toxicity thereof, causing diseases such as atopic dermatitis or seborrheic dermatitis.

However, in the invention of the present application, the surfactant is not used, but distilled *Chamaecyparis obtusa* water extracted from *Chamaecyparis obtusa* trees is used, thus securing cleansing effects, such as a deodorization effect of eliminating smells from the ear of the companion animal, an antibacterial effect of inhibiting the growth of mold and eliminating bacteria such as *Escherichia coli* or *Staphylococcus aureus*, and an exfoliation effect of eliminating corneous cells of the skin. Accordingly, it is possible to develop an ear-cleansing agent for companion animals that does not irritate the ears of companion animals.

The ear-cleansing agent for companion animals according to the embodiment of the present invention includes a solvent, a humectant, a pH adjuster, a sterilization adjuster, and an exfoliating agent in the distilled *Chamaecyparis obtusa* water. Purified water is used as the solvent, glycerin and panthenol are used as the humectant, malic acid and tromethamine are used as the pH adjuster, benzoic acid is used as a sterilizing preservative, and salicylic acid is used as the exfoliating agent.

The ear-cleansing agent for companion animals includes 46 to 50 parts by weight of the distilled *Chamaecyparis obtusa* water, 40 to 55 parts by weight of the purified water, 3 to 7 parts by weight of the glycerin, 0.3 to 0.6 parts by weight of the panthenol, 1 to 3 parts by weight of the malic acid, 1 to 3 parts by weight of the tromethamine, 0.1 to 0.2 parts by weight of the benzoic acid, and 0.02 to 0.06 parts by weight of the salicylic acid.

Glycerin ($C_3H_5(OH)_3$) is also called glycerol and has a melting point of 17.8° C. and a boiling point of 290° C. Glycerin is a colorless and odorless liquid having a very high viscosity, may be used as a preservative, an anti-drying agent, and a sweetener for foods, and is widely used as an anti-drying agent for cosmetics. When glycerin is used as an external medicine, it may be applied after dilution or may be used as an ointment. In the present invention, glycerin is used as a humectant.

Panthenol ($C_9H_{19}NO_4$) is a colorless liquid having a density of 1.2 g/ml, a melting point of 66 to 69° C., and a boiling point of 118 to 120° C. Panthenol is a sticky hygroscopic liquid and serves as a wetting agent, a softening agent, and a humectant. Panthenol enhances the moisturizing and maintaining function of the skin and stimulates regeneration of the skin. It makes dry skin smooth and elastic, and is frequently used to prevent inflammation and itching. Panthenol is used as the humectant in the present invention.

Malic acid ($C_4H_6O_5$) is also called apple acid, is contained in natural fruits such as apples and grapes, and has a needle-shaped crystal form. Malic acid has a melting point of 98 to 99° C. and a boiling point of 140° C., and is soluble in water, ethanol, and acetone. Malic acid is used as the pH adjuster in the present invention.

Tromethamine ($C_4H_{11}NO_3$) is a tris(hydroxymethyl)aminomethane or tris(hydroxymethyl)aminomethine, and is simply referred to as "tris". Tromethamine is a white crystalline powder having a melting point of 175° C. and a boiling point of 219° C., and is used for the purpose of pH and scent adjustment in cosmetics. The tromethamine is used as the pH adjuster in the present invention.

Benzoic acid ($C_7H_6O_2$) has the form of scaly or needle-shaped crystals, a melting point of 122° C., and a boiling point of 250° C. Benzoic acid is not easily dissolved in cold water, but is readily soluble in hot water and in general organic solvents such as acetone, ethanol, and ether. Benzoic acid is one of the synthetic preservatives approved by the Food Hygiene Law, the preservative effect thereof markedly depends on the pH of the food, and the efficacy thereof is increased when the pH is acidic. Benzoic acid is used as the sterilizing preservative in the present invention.

Salicylic acid ($C_7H_6O_3$) has the form of needle-shaped crystals, is a white solid having a melting point of 159° C. and a boiling point of 211° C., and is soluble in water. Salicylic acid is generally used as a keratolytic agent and a medicine for skin diseases, and is also used as a preservative for foods under the Food Hygiene Law. Salicylic acid is used as the exfoliating agent in the present invention.

According to another embodiment of the present invention, a method of manufacturing an ear-cleansing agent for companion animals according to the present invention includes a heating-agitation step of performing heating while mixing purified water, malic acid, benzoic acid, and salicylic acid to perform dissolution, a cooling-agitation step of cooling and agitating a mixed solution obtained after the heating-agitation step is completed, and a raw-material-mixing step of mixing the cooled and agitated mixed solution with distilled *Chamaecyparis obtusa* water, glycerin, panthenol, and tromethamine with heating and agitation.

During the heating-agitation step, heating to 75 to 85° C. is performed. The purified water is included in a content of 40 to 55 parts by weight, the malic acid is included in a content of 1 to 3 parts by weight, the benzoic acid is included in a content of 0.3 to 0.6 parts by weight, and the salicylic acid is included in a content of 0.02 to 0.06 parts by weight. The malic acid, the benzoic acid, and the salicylic acid mixed during the heating-agitation step exist in a crystalline form, and are heated to dissolve the same in water. However, the efficacy thereof is not reduced even when heated.

The cooling-agitation step is a step of cooling and agitating the mixed solution obtained by mixing during the heating-agitation step, and cooling to 30 to 38° C. is performed. When the raw materials to be mixed during the subsequent raw-material-mixing step are at high temperatures, the efficiency thereof is reduced due to the heat. Accordingly, the cooling process is performed before mixing the raw materials.

The raw-material-mixing step is a step of mixing the cooled and agitated mixed solution with the distilled *Chamaecyparis obtusa* water, the glycerin, the panthenol, and the tromethamine with agitation. 46 to 50 parts by weight of the distilled *Chamaecyparis obtusa* water, 3 to 7 parts by weight of the glycerin, 0.3 to 0.6 parts by weight of the panthenol, and 1 to 3 parts by weight of tromethamine are included and mixed. When the content of the distilled *Chamaecyparis obtusa* water is maintained below 46 parts by weight, the antibacterial, deodorization, and exfoliation efficacies are reduced. When the content is greater than 50 parts by weight, the skin is irritated and inflammation is caused.

According to another embodiment of the present invention, a filtration step of eliminating foreign materials from a mixture obtained after the raw-material-mixing step is completed is further included. During the filtration step, the foreign materials are filtered by passing the mixture through a mesh net. Preferably, the mesh net of 300 mesh is used.

MODE FOR INVENTION

Hereinafter, preferred Examples and Experimental Examples are shown to facilitate understanding of the present invention. However, the following Examples and Experimental Examples are provided only for the purpose of easier understanding of the present invention, and the content of the present invention is not limited by the Examples.

Example 1

(1) 40 parts by weight of purified water, 2.3 parts by weight of malic acid, 0.15 parts by weight of benzoic acid, and 0.04 parts by weight of salicylic acid were prepared and added to an emulsification tank, followed by heating to a temperature of 80° C. with agitation.

(2) After the above-mentioned raw materials were mixed, the temperature was lowered to 35° C., and heating was performed with agitation.

(3) 48 parts by weight of distilled *Chamaecyparis obtusa* water, 5 parts by weight of glycerin, 0.5 parts by weight of panthenol, and 1 part by weight of tromethamine were prepared and added to an emulsification tank, followed by mixing.

(4) The mixture was passed through a 300-mesh net to thus be filtered, thereby manufacturing an ear-cleansing agent for companion animals.

Comparative Example 1

The ear-cleansing agent was manufactured using the same condition as in Example 1 except that the distilled *Chamaecyparis obtusa* water was not added.

Comparative Example 2

The ear-cleansing agent was manufactured under the same conditions as in Example 1 except that 45 parts by weight of the distilled *Chamaecyparis obtusa* water was included.

<Experiment 1> Skin Irritation Experiment (1) Three albino rabbits (supplied by NARA Biotech, male) were prepared and subjected to acclimatization in an animal room in which a test was performed for 5 days or more, and general symptoms were observed at least once a day (temperature 23±2° C., relative humidity 50±20%, number of ventilation 10 to 15 times/hr, and lighting cycle 12 hours, 8:00 am on-8:00 pm off).

(2) 24 hours before application of the Example 1, the dorsal skin of the rabbit was epilated using an electric epilator so as to prevent injury, and a piece of gauze that was coated with Example 1 and had a size of 2×3 cm in width and height was brought into contact with the epilated skin. The gauze was wrapped with a non-permeable and low-irritation medical tape, and was removed after 4 hours.

(3) 5 hours (which was about 1 hour after the elimination of Example 1), 24 hours, 48 hours, and 72 hours after the application of Example 1, changes including erythema, incrustation, and edema were observed. The occurrence of erythema, incrustation, and edema were judged by the naked eye, and edema was judged with mild palpation. The results are shown in Table 1 and FIG. 1 below.

The evaluation criteria of the skin reaction are as follows.

1) Formation of Erythema and Eschar

The case of no erythema and eschar was marked as 0, the case of very mild erythema was marked as 1, the case of distinct erythema was marked as 2, the case of slightly severe erythema was marked as 3, and the case of severe erythema was marked as 4.

2) Formation of Edema

The case of no edema was marked as 0, the case of very mild edema (almost visible to the naked eye) was marked as 1, the case of mild edema (clearly distinguished by swelling) was marked as 2, the case of advanced edema (swelling of about 1 mm) was marked as 3, and the case of severe edema (swelling of more than 1 mm and extending to the outside of the exposed part) was marked as 4.

3) Primary Irritation Index (P.I.I.)

0.0 to 0.5 non-irritant, 0.6 to 2.0 weakly irritant, 2.1 to 5.0 moderately irritant, 5.1 to 8.0 strongly irritant

TABLE 1

|  | Rabbit 1 | | Rabbit 2 | | Rabbit 3 | |
| --- | --- | --- | --- | --- | --- | --- |
| Time | Formation of erythema and eschar | Formation of edema | Formation of erythema and eschar | Formation of edema | Formation of erythema and eschar | Formation of edema |
| 5 hours | 0 | 0 | 0 | 0 | 1 | 0 |
| 24 hours | 0 | 0 | 0 | 0 | 1 | 0 |
| 48 hours | 0 | 0 | 0 | 0 | 0.5 | 0 |
| 72 hours | 0 | 0 | 0 | 0 | 0 | 0 |

As shown in Table 1, from the result of judgment of irritation, it can be seen that eschar and edema were not formed in rabbits 1 and 2 and that weak erythema and eschar were observed in rabbit 3.

It can be seen that the primary skin irritation index (PII), which was an average calculated by summing the irritation indexes of rabbits 1, 2, and 3, was 0.33 after 5 hours, 0.33 after 24 hours, 0.17 after 48 hours, and 0.0 after 72 hours.

Accordingly, it can be seen that the degree of skin irritation as a whole corresponds to non-irritation, and in particular, after 72 hours, skin irritation completely disappears, thus corresponding to non-irritation.

<Experiment 2> Deodorization Effect Test (1) The deodorization effect test was conducted at a temperature of 25.1±0.5° C. and a humidity of 42.8±1.1% R.H.

(2) 20 mL of Example 1 was placed in a 5 L reactor, followed by sealing. Then, ammonia gas was injected at 50 μmol/mol, and measurement was performed after the lapse of 0, 30, 60, 90, and 120 minutes using a gas detector tube (former KS2218:2009).

Figure 2:
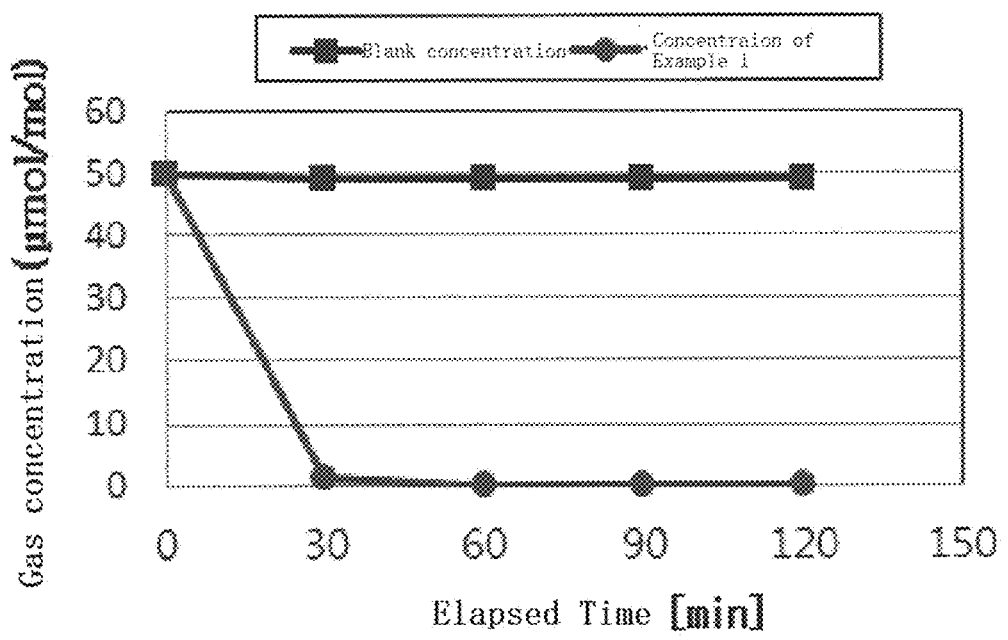
FIG. 2 is a graph showing the result of an experiment on an ammonia-gas deodorization effect when an ear-cleansing agent for companion animals according to the present invention is used.

(3) Ammonia gas was injected at 50 μmol/mol into a 5 L reactor with nothing added thereto (blank), and measurement was performed after the lapse of 0, 30, 60, 90, and 120 minutes using a gas detector tube (former KS2218:2009). The results are shown in Table 2 and FIG. 2 below.

TABLE 2

| | Blank concentration (μmol/mol) | Example concentration (μmol/mol) | Deodorization rate (%) |
|---|---|---|---|
| 0 minutes | 50 | 50 | 0.0 |
| 30 minutes | 49 | 1 | 98.0 |
| 60 minutes | 49 | <0.2 | 99.6 |
| 90 minutes | 49 | <0.2 | 99.6 |
| 120 minutes | 49 | <0.2 | 99.6 |

Detection limit 0.2 μmol/mol

Deodorization rate (%)=[{blank concentration)−(specimen concentration))}/(blank concentration)]×100

As shown in Table 2, when the Example according to the present invention is used, it can be seen that the added ammonia gas is eliminated within a short time, for example, a deodorization rate of 98% within 30 minutes. On the other hand, in the case of the blank with nothing added, it can be seen that ammonia remains in the reactor.

Therefore, it can be seen that Example 1 has an excellent deodorization effect.

<Experiment 3> Antibacterial Experiment

1. Antifungal Test (1) The test environment was (29.0±0.1°) C. and (96.7±0.5)% R.H.

(2) Inoculation with a test-strain-mixed-spore solution was performed in Example 1, followed by leaving for 24 hours and then incubation for 5 days, to measure whether mold grew. The strains used were *Aspergillus niger* ATCC9642, *Penicillium pinophilum* ATCC 11797, *Chaetomium globosum* ATCC 6205, *Gliocladium virens* ATCC 9645, and *Aureobasidium pullulans* ATCC 15233. The results are shown in Table 3 and FIG. 3 below.

TABLE 3

| Test item | Test result |
|---|---|
| Antifungal test | 0 |

Figure 3:
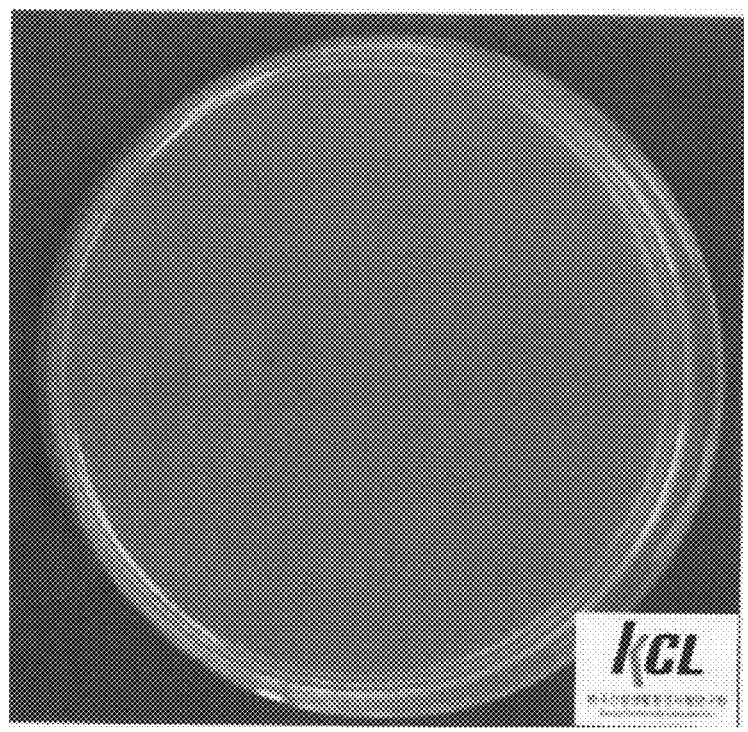
FIG. 3 is a photograph showing an experiment for inhibiting mold growth.

As shown in Table 3, it can be seen that the mold did not grow at all upon inoculation with the test-strain-mixed-spore solution in Example 1 (see FIG. 3).

Therefore, it can be seen that Example 1 inhibits mold growth.

2. *Escherichia coli* Elimination Test (1) The test environment was (37±0.1°) C. and (34.2±0.2)% R.H.

(2) *Escherichia coli* was tested according to a KCL-FIR-1002:2011 test method, *Escherichia coli* ATCC 25922 was used as a strain, and the concentration of inoculation bacteria (CFU/mL) was $1.6 \times 10^6$.

Figure 4:
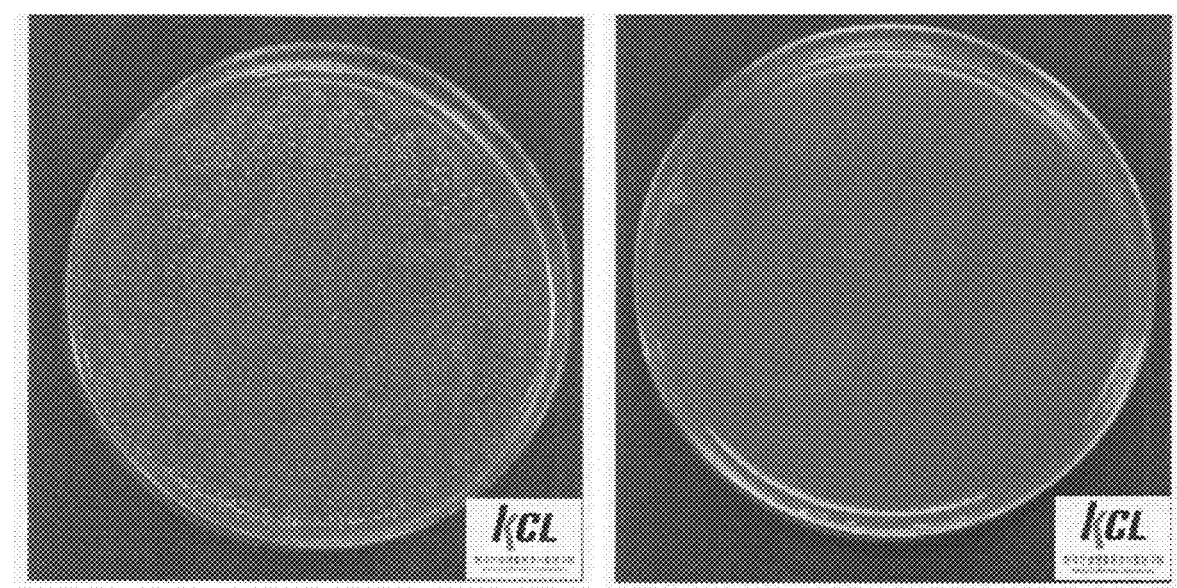
FIG. 4 is a photograph showing the results of Example 1 (1) and a blank (2) in an experiment for eliminating *Escherichia coli*.

(3) The concentration after 24 hours is shown in Table 4 below, and a photograph of the result thereof is shown in FIG. 4.

TABLE 4

| | Initial concentration (CFU/mL) | Concentration after 24 hours (CFU/mL) | Bacterial reduction rate (%) |
|---|---|---|---|
| Blank | $1.6 \times 10^4$ | $7.1 \times 10^4$ | — |
| Example 1 | $1.6 \times 10^4$ | <10 | 99.9 |
| Comparative Example 1 | $1.6 \times 10^4$ | $1.4 \times 10^4$ | 12.5 |
| Comparative Example 2 | $1.6 \times 10^4$ | $7.3 \times 10^3$ | 54.4 |

[CFU: Colony Forming Unit]

As shown in Table 4, it can be seen that the concentration of *Escherichia coli* was reduced after 24 hours (see (2) in FIG. 4) in the case of Example 1 but was increased in the case of the blank with nothing added (see (1) in FIG. 4).

In addition, in the case of Comparative Example 1, in which distilled *Chamaecyparis obtusa* water was not added, it can be seen that the concentration of *Escherichia coli* was reduced by about 12.5% but that the bacterial reduction rate was remarkably lower than that of Example 1.

Further, in the case of Comparative Example 2, which included 45 parts by weight of the distilled *Chamaecyparis obtusa* water, it can be seen that the concentration of *Escherichia coli* was reduced by 54.4%, thus eliminating *Escherichia coli* to some extent, but the effect thereof was lower than that of Example 1.

Therefore, it can be seen that there is a difference in the effect of eliminating *Escherichia coli* depending on the concentration of the distilled *Chamaecyparis obtusa* water.

3. *Staphylococcus aureus* Elimination Test (1) The test environment was (37±0.1°) C. and (34.2±0.2)% R.H.

(2) A *Staphylococcus aureus* elimination test was performed according to a KCL-FIR-1002:2011 test method, *Staphylococcus aureus* ATCC 6538 was used as a strain, and the concentration of inoculation bacteria (CFU/mL) was $1.1 \times 10^6$.

Figure 5:
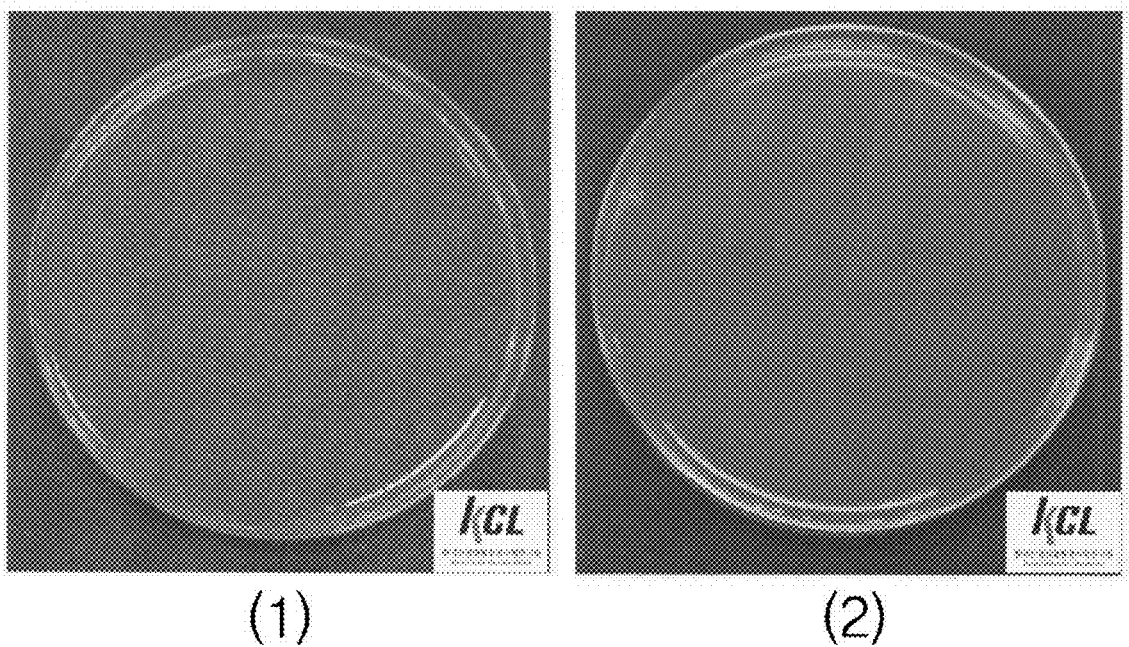
FIG. 5 is a photograph showing the results of Example 1 (1) and a blank (2) in an experiment for eliminating *Staphylococcus aureus*.

(3) The concentration after 24 hours is shown in Table 5 below, and a photograph of the result thereof is shown in FIG. 5.

TABLE 5

| | Initial concentration (CFU/mL) | Concentration after 24 hours (CFU/mL) | Bacterial reduction rate (%) |
|---|---|---|---|
| Blank | $1.1 \times 10^4$ | $3.9 \times 10^4$ | — |
| Example 1 | $1.1 \times 10^4$ | <10 | 99.9 |
| Comparative Example 1 | $1.1 \times 10^4$ | $9.9 \times 10^3$ | 10.0 |
| Comparative Example 2 | $1.1 \times 10^4$ | $4.9 \times 10^3$ | 55.5 |

[CFU: Colony Forming Unit]

As shown in Table 4, it can be seen that the concentration of *Escherichia coli* was reduced after 24 hours (see (2) in FIG. 5) in the case of Example 1 but was increased in the case of the blank with nothing added thereto (see (1) in FIG. 5).

In addition, in the case of Comparative Example 1, in which distilled *Chamaecyparis obtusa* water was not added, it can be seen that the concentration of *Escherichia coli* was reduced to some extent but that the bacterial reduction rate was remarkably lower than that of Example 1.

Further, in the case of Comparative Example 2, including 45 parts by weight of the distilled *Chamaecyparis obtusa* water, it can be seen that the concentration of *Escherichia* coli was reduced by 55.5%, thus eliminating *Escherichia coli* to some extent, but the effect thereof was lower than that of Example 1.

Therefore, it can be seen that there is a difference in the effect of eliminating *Staphylococcus aureus* depending on the concentration of the distilled *Chamaecyparis obtusa* water.

<Experimental Example 4> Exfoliation Experiment (1) After 15 subjects in their 20s to 40s were classified into 3 groups as Example 1, Comparative Example 1, and Comparative Example 2, Example 1, Comparative Example 1, and Comparative Example 2 were respectively applied to the elbows of the persons in each group. The subjects were prohibited from applying body lotion or cosmetics to the corresponding area, which could affect the test results, starting three weeks before the test.

(2) The image of the skin state before and after use was photographed and analyzed using a Visioscan (VC98 Courage & Khazaka, Germany), the measured values were recorded, and the degree of exfoliation was confirmed before and after use. The results are shown in Table 6 below.

TABLE 6

|  | Before use | After use |
| --- | --- | --- |
| Example 1 | 3.3 | 0.5 |
| Comparative Example 1 | 3.4 | 3.1 |
| Comparative Example 2 | 3.2 | 1.0 |

As shown in Table 6, it can be seen that the degree of exfoliation was greatly reduced after the use of Example 1 but that Comparative Example 1, which did not include the distilled *Chamaecyparis obtusa* water, showed no significant change in exfoliation. Further, it can be seen that the exfoliation efficacy was lower in Comparative Example 2, including 45 parts by weight of the distilled *Chamaecyparis obtusa* water, than in Example 1.

Thus, it can be seen that there is a difference in exfoliation efficacy depending on the concentration of the distilled *Chamaecyparis obtusa* water.

[Review]

The skin irritation experiment showed that the degree of skin irritation was stable in Example 1, including the distilled *Chamaecyparis obtusa* water. Accordingly, it is considered that the skin is not irritated.

Further, excellent efficacy in removing ammonia odors was observed. Accordingly, it is considered that a deodorization effect is secured.

Further, the antifungal test, the *Escherichia coli* elimination test, and the *Staphylococcus aureus* elimination test showed that mold growth was inhibited, and the efficacy of eliminating *Escherichia coli* and *Staphylococcus aureus* was excellent. Accordingly, it is considered that an antibacterial effect is secured.

Further, the exfoliation experiment showed that the exfoliation efficacy was excellent in Example 1. Accordingly, it is considered that an exfoliation effect is secured.

Therefore, based on the above-mentioned results, it is considered that the antibacterial effect, the deodorization effect, and the exfoliation effect are secured when the distilled *Chamaecyparis obtusa* water is included, and as a result, the distilled *Chamaecyparis obtusa* water is usable in an ear-cleansing agent for companion animals containing no surfactant.

The invention claimed is:

1. An ear-cleansing agent for companion animals, comprising:
    a *Chamaecyparis obtusa* sap extracted from *Chamaecyparis obtusa* trees as an effective component, wherein the *Chamaecyparis obtusa* sap is distilled *Chamaecyparis obtusa* water; and
    purified water as a solvent, glycerin and panthenol as a humectant, malic acid and tromethamine as a pH adjuster, benzoic acid as a sterilizing preservative, and salicylic acid as an exfoliating agent, so that antibacterial action, deodorization, and exfoliation are capable of being performed without irritating a skin even when the ear-cleansing agent is not washed away using water,
    wherein the ear-cleansing agent includes 46 to 50 parts by weight of the distilled *Chamaecyparis obtusa* water, 40 to 55 parts by weight of the purified water, 3 to 7 parts by weight of the glycerin, 0.3 to 0.6 parts by weight of the panthenol, 1 to 3 parts by weight of the malic acid, 1 to 3 parts by weight of the tromethamine, 0.1 to 0.2 parts by weight of the benzoic acid, and 0.02 to 0.06 parts by weight of the salicylic acid.

2. The ear-cleansing agent of claim 1, wherein the distilled *Chamaecyparis obtusa* water is extracted via steps of:
    drying the *Chamaecyparis obtusa* trees in a dryer and then cutting the dried *Chamaecyparis obtusa* trees to perform powderization;
    placing the powderized *Chamaecyparis obtusa* trees in a distillation tank to thus supply a distilled water;
    heating the distillation tank to thus supply steam to the powderized *Chamaecyparis obtusa* trees so that a water vapor containing a component extracted from the steam is moved to a cooler, thus extracting a *Chamaecyparis obtusa* oil and the distilled *Chamaecyparis obtusa* water; and
    separating and extracting the distilled *Chamaecyparis obtusa* water from an extract obtained by extracting the *Chamaecyparis obtusa* oil and the distilled *Chamaecyparis obtusa* water.

* * * * *